United States Patent [19]

Saito

[11] Patent Number: 5,739,051
[45] Date of Patent: Apr. 14, 1998

[54] METHOD AND DEVICE FOR DETECTING THE END POINT OF PLASMA PROCESS

[75] Inventor: Susumu Saito, Yamanashi-ken, Japan

[73] Assignee: Tokyo Electron Limited, Tokyo, Japan

[21] Appl. No.: 715,489

[22] Filed: Sep. 18, 1996

Related U.S. Application Data

[63] Continuation of Ser. No. 205,806, Mar. 4, 1994, abandoned.

[30] Foreign Application Priority Data

| Mar. 4, 1993 | [JP] | Japan | 5-069204 |
| Mar. 4, 1993 | [JP] | Japan | 5-069205 |

[51] Int. Cl.$^6$ .................... H01L 21/00; C23C 16/00
[52] U.S. Cl. .................... 438/16; 438/9; 216/60; 204/298.03; 204/298.32; 156/345; 118/723 R
[58] Field of Search ............. 156/626.1, 643.1, 156/345; 216/60, 67; 204/298.32, 298.03; 118/723 R, 723 E; 438/7, 8, 9, 16, 101, 102

[56] References Cited

U.S. PATENT DOCUMENTS

| 4,482,424 | 11/1984 | Katzir et al. | 156/626 |
| 4,491,499 | 1/1985 | Jerde et al. | 156/626 |
| 4,541,718 | 9/1985 | Osada et al. | 356/316 |
| 4,615,761 | 10/1986 | Tada et al. | 156/626 |
| 4,687,539 | 8/1987 | Burns et al. | 156/626 |
| 4,846,928 | 7/1989 | Dolins et al. | 156/626.1 |
| 4,948,458 | 8/1990 | Ogle . | |
| 5,118,378 | 6/1992 | Moroi et al. | 156/345 |
| 5,160,576 | 11/1992 | Robbins | 156/626 |
| 5,226,967 | 7/1993 | Chen et al. . | |
| 5,232,537 | 8/1993 | Yachi | 156/626.1 |
| 5,241,245 | 8/1993 | Barnes et al. . | |
| 5,290,383 | 3/1994 | Koshimizu | 156/345 |
| 5,320,704 | 6/1994 | Horioka et al. | 156/626 |
| 5,322,590 | 6/1994 | Koshimizu | 156/626 |

FOREIGN PATENT DOCUMENTS

| 0 379 828 | 8/1990 | European Pat. Off. . | |
| 511448 | 11/1992 | European Pat. Off. | 156/626.1 |
| 4-290428 | 10/1992 | Japan . | |
| 5-206072 | 8/1993 | Japan . | |

*Primary Examiner*—R. Bruce Breneman
*Assistant Examiner*—Luz Alejandro
*Attorney, Agent, or Firm*—Oblon, Spivak, McClelland, Maier & Neustadt, P.C.

[57] ABSTRACT

Method and device for detecting the end point of a plasma process, the method and device being capable of making it unnecessary to set a threshold every process or every processed object and also capable of correctly detecting the end point of the plasma process even if process conditions are changed. The method and device can be therefore used for more purposes. According to the end point detecting method realized by the end point detecting device, the emission spectrum of an active species having a specific wavelength and caused when a semiconductor wafer W is processed with plasma P is detected by a photodetector and the end point of the plasma process is detected on the basis of light strength changes of the emission spectrum. More specifically, an average value m and dispersed ones $\sigma^2$ of light strengths I are calculated for a predetermined time period $T_1$ at the initial process stage by a first arithmetical unit and the differences of light strengths I relative to the average value m are calculated after the lapse of the predetermined time period $T_1$ by a second arithmetical unit. These differences are compared with the dispersed values $\sigma^2$ by a comparator and the time at which values thus obtained exceed a predetermined reference value is decided to be the end point of the plasma process.

11 Claims, 7 Drawing Sheets

S : CHANGE-START POINT
E : CHANGE-END POINT

METHOD AND DEVICE FOR DETECTING THE END POINT OF PLASMA PROCESS

This application is a continuation of application Ser. No. 08/205,806, filed on Mar. 4, 1994, now abandoned.

BACKGROUND OF THE INVENTION

1. Field of the Invention

The present invention relates to method and device for detecting the end point of plasma process.

2. Description of the Related Art

The etching apparatus in which plasma is used has been variously incorporated into the course of manufacturing semiconductor devices, and substrates for liquid crystal display devices. It includes upper and lower electrodes arranged parallel to each other and it is intended to etch semiconductor wafers with active species in plasma while discharging between the upper and the lower electrode to make etching gas into plasma. When the semiconductor wafer is being etched, the progress of the etching process is observed and the end point of it is as correctly detected as possible to pattern the wafer as desired.

Conventionally, instrumental analysis methods such as mass spectrometry and spectroscopic analysis are used to detect the end point of etching process. Relatively simple and high sensitive one of them is the spectroscopic analysis. When the spectroscopic analysis is used, a specific active species is selected from radicals, ions and others of etching gas, its decomposed and reacted products and light strengths of the emission spectrum of this active species selected are measured The active species selected depends upon the kind of etching gas in this case. When etching gas of the fluorocarbon series such as $CF_4$ is used to etch silicon oxide film, spectrum (219 nm, 483.5 nm or others) emitted from the reacted product $CO^*$ is measured. When the fluorocarbon series etching gas such as $CF_4$ is used to etch silicon nitride film, spectrum (674 nm or others) emitted from the reacted product $N^*$ is measured. The end point of etching process is decided by comparing changing values, which represent the light strength of the above-mentioned active species having a specific wavelength and primary and secondary differential ones of these light strength values, with a threshold previously set.

In the case of the conventional end point detecting methods, however, the active species whose spectrum is measured must be changed depending upon the kind of process used and also the kind of film etched. The threshold, therefore, must also be changed every active species used. Further, when films to be etched belong to the same kind but they are different in thickness, the etching condition under which one of them is etched must be changed from that for the other. This makes it necessary to change the threshold to meet the etching condition changed. In short, the threshold must be changed every etching condition employed, under different etching condition. It needs complexed calculations to set the threshold.

SUMMARY OF THE INVENTION

The present invention is therefore intended to the above-mentioned drawbacks.

Accordingly, the object of the present invention is to provide an end point detecting method and a device for the same, capable of making it unnecessary to change the threshold every process used and every matter processed and also capable of more correctly detecting the end point of plasma process even if the process condition is changed.

This object of the present invention can be achieved by a method of detecting the end point of a plasma process comprising continuously detecting the emission spectrum of an active species in plasma which has a specific wavelength by means of photodetector means when an object is processed with plasma; calculating an average value and dispersed ones from a light strengths of the emission spectrum for a predetermined time period at the initial process stage; calculating their differences relative to the average value from a light strengths after the lapse of the predetermined time period; and comparing values thus arithmetically calculated with the dispersed ones and deciding the end point of the plasma process when the arithmetically-calculated values exceed a predetermined reference value.

The object of the present invention can also be attained by a device for detecting the end point of a plasma process comprising first arithmetical means for calculating an average value and dispersed ones of light strengths, said light strengths being obtained by detecting the emission spectrum of an active species, which has a specific wavelength and which is caused when an object is process with plasma, by photodetector means; second arithmetical means for calculating the differences of said light strengths relative to the average value obtained by the first arithmetical means; comparator means for comparing values obtained by the second arithmetical means with the dispersed ones obtained by the first arithmetical means; and decision means for deciding the time at which values obtained by the comparator means exceed a predetermined reference value to be the end point of the plasma process; wherein the end point of the plasma process is detected on the basis of light strength change of the emission spectrum.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 8A and 8B are intended to explain the operation of the end point detecting device in FIG. 6, in which

FIGS. 10A and 10B are intended to explain another operation of the end point detecting device in FIG. 6, in which

FIGS. 11A and 11B are intended to explain a further operation of the end point detecting device in FIG. 6, in which

FIGS. 13A through 13C are intended to explain a still further operation of the end point detecting device in FIG. 6, in which

DETAILED DESCRIPTION OF THE PREFERRED EMBODIMENTS

According to the present invention, emission spectra are detected one after the other by photodetector means, an emission spectrum having a specific wavelength is separated from these emission spectra, and an average value of light strengths of this emission spectrum and dispersed values of them are calculated and stored for a predetermined time period $T_1$ from the start of a plasma process. After the lapse of this predetermined time period $T_1$, the difference of the above-mentioned average value relative to a value representing a light strength then obtained is calculated and it is compared with the disperse values. When the value thus obtained exceeds a reference value, it is decided that the plasma process is finished. In short, this time tells the end point of the plasma process. An example of the present invention will be described in detail with reference to the accompanying drawings.

EXAMPLE 1

Figure 1:
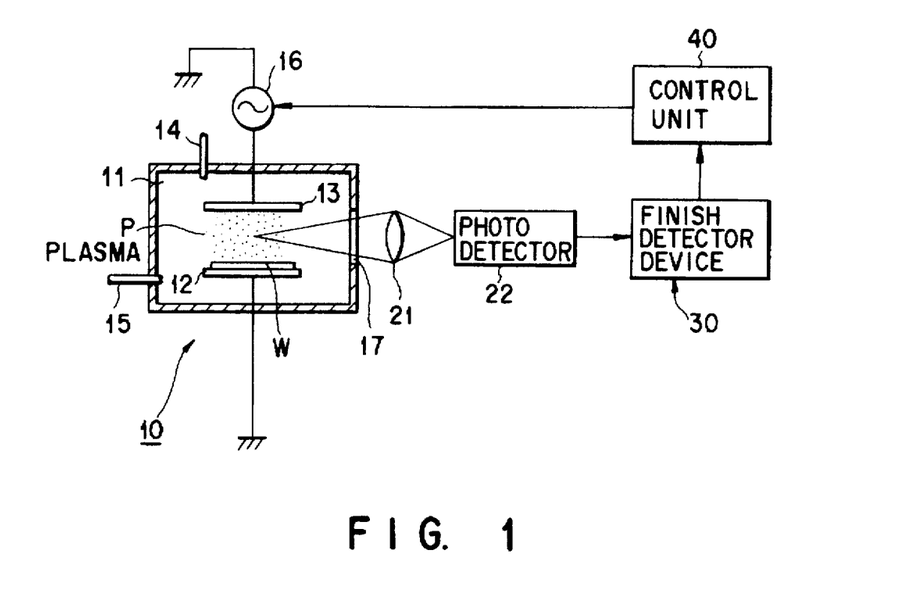
FIG. 1 is a view showing the main portion of a plasma process apparatus provided with the end point detecting device according to an embodiment of the present invention.

FIG. 1 shows the plasma process apparatus to which an end point detecting device according to the present invention is provided. This plasma process apparatus 10 comprises a process chamber 11 made of conductive material such as aluminium, a lower electrode 12 arranged in the process chamber 11 and serving as a susceptor on which an object such as a semiconductor wafer W to be processed is placed, and an upper electrode 13 arranged above the lower one 12 with an interval between them.

A gas supply pipe 14 is connected to the top of the process chamber 11 to introduce etching gas of the fluorocarbon series such as $CF_4$ into the chamber 11 through it. An exhaust pipe 15 is also connected to a side of the chamber 11 to exhaust gases generated outside the chamber 11 through it. The lower electrode 12 is electrically grounded and it is thus kept to have ground potential. The upper electrode 13 is connected to a high frequency power source 16. High frequency voltage is applied to the upper electrode 13 from the power source 16 to discharge between the upper 13 and the lower electrode 12. The etching gas in the chamber 11 is thus activated to generate plasma P which includes active species such as radicals and ions.

A window 17 made of transparent material such as quartz glass is attached to that side of the process chamber 11 which is opposed to the exhaust-pipe-connected side thereof. The emission spectra of plasma P are passed through the window 17 and analyzed to check the etching process. A lens 21 is arranged outside and behind the window 17 to collect the emission spectra thus passed. A photodetector 22 is further arranged behind the lens 21 to detect and photoelectrically convert the emission spectra thus collected. The photodetector 22 comprises an interference filter or spectroscope, and a photodiode or a photomultiplier, for example. The emission spectrum having a specific wavelength is separated from the emission spectra by the interference filter or spectroscope and it is photoelectrically converted into a signal which denotes its light strength. Responsive to this signal applied from the photodetector 22, the end point detecting device 30 which will be described later detects the end point of the etching process and send control signal to a control unit 40. Responsive to control signal thus applied, the control unit 40 controls the plasma process apparatus 10 to end the etching process.

The lens 21 can be moved by lens driver means 21a. When the emission spectrum having a specific wavelength is to be detected in a case where film on a semiconductor substrate is to be etched, light reflected by the top surface of film interferes with one reflected by the bottom surface (or interface of film relative to the semiconductor substrate) of film. This makes it impossible to accurately detect the light strength of the emission spectrum. This, however, can be prevented when a focus point of the lens 21 can be moved, as desired, by the lens driver means 21a. The thickness of film changes as etching process advances. It is therefore desirable that the lens 21 is moved to change its focus point as the film thickness reduces.

Figure 2:
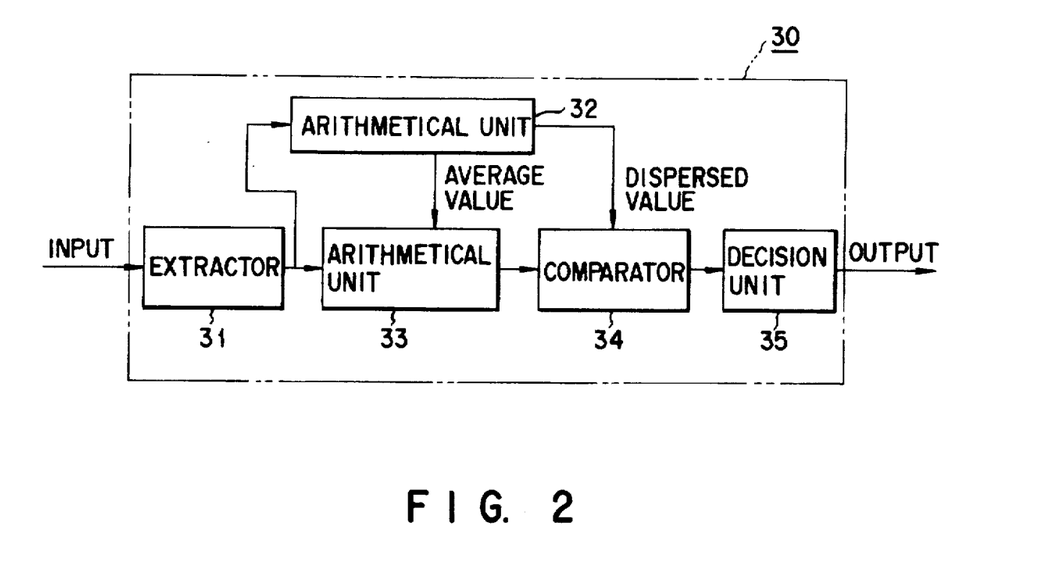
FIG. 2 is a block diagram showing the end point detecting device in FIG. 1.

The end point detecting device 30 according to the present invention will be described with reference to FIGS. 1 through 4. As shown in FIG. 2, it comprises an extractor 31 for extracting elements such as light strength I and linear differential value (or slope) of the waveform from signal or waveform of light strength I applied from the photodetector 22, an arithmetical unit 32 for calculating an average value m and dispersed values $\sigma^2$ from light strengths I (see FIG. 3) extracted one after another by the extractor 31, another arithmetical unit 33 for calculating the difference of average value m applied from the arithmetical unit 32 relative to light strengths I applied from the extractor 31, a comparator 34 for comparing the values of difference applied from the arithmetical unit 33 with dispersed values $\sigma^2$ applied from the arithmetical unit 32, and a decision unit 35 for deciding the end point of etching process when the absolute-value of compared values applied from the comparator 34 exceeds a predetermined reference value. The decision made by the decision unit 35 is applied to a control unit 40, which controls the high frequency power source 16 and others, responsive to signal thus applied, to thereby control etching process.

It will be described how the end point of an etching process is detected by the end point detecting device according to the present invention. The average value m and dispersed ones $\sigma^2$ which represent light strengths I of plasma P for the predetermined time period $T_1$ are calculated at the initial etching stage by the arithmetical unit 32. The amount of etching gas to be used and the irregularity of light strengths I caused by electric noises are thus statistically grasped or checked from these values. After the lapse of the predetermined time period $T_1$, the difference of the average value m relative to the light strength I, which changes as time goes by, is calculated by the arithmetical unit 33. The difference values are then compared with the dispersed values $\sigma^2$ by the comparator 34. When an absolute-value thus obtained exceeds the reference value, the decision unit 35 decides that the etching process is finished.

Figure 3:
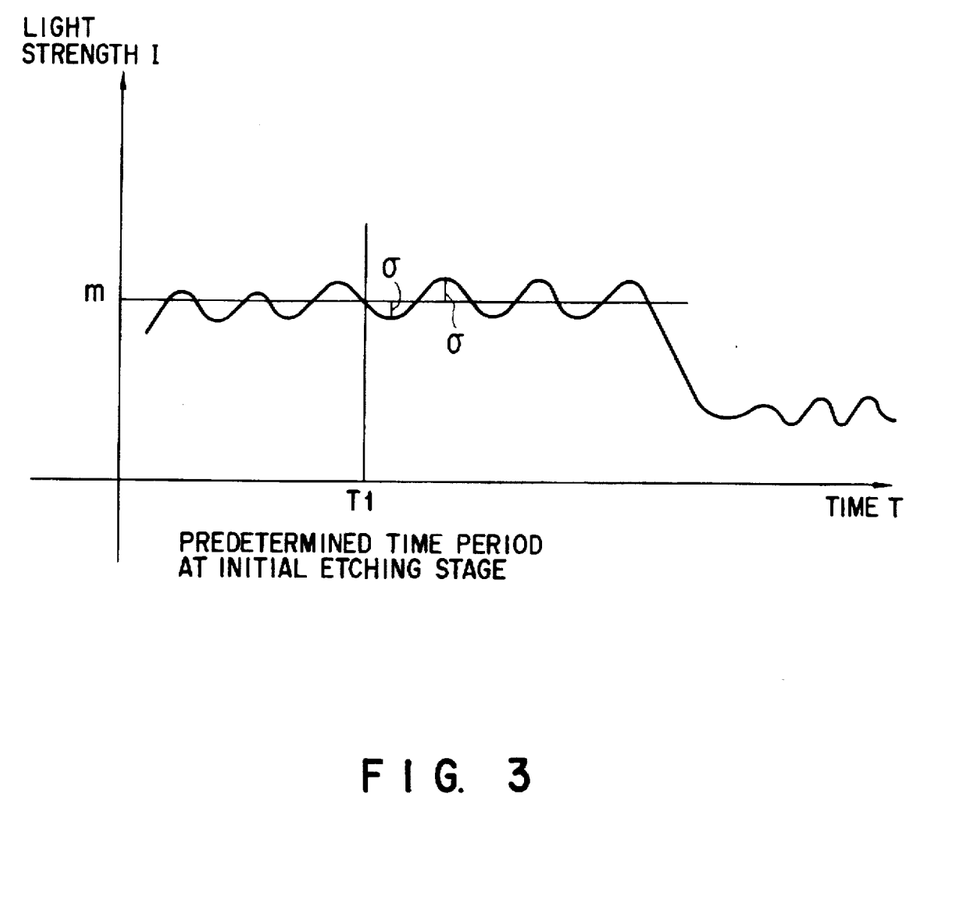
FIG. 3 is a graph intended to explain the operation of the end point detecting device in FIG. 1.

The predetermined time period $T_1$ at the initial etching stage is a certain time length optionally set from the start to the end of the etching process, and it is not under the control of etching conditions but common to various kinds of etching processes. When the average value m and dispersed ones $\sigma^2$ are obtained in this manner from the waveform of light strengths I which change for the predetermined time period $T_1$, the upper and the lower value of light strengths I which change as etching process advances can be checked or grasped at the initial etching stage. When the values of difference obtained between light strengths I and the average value m are compared directly with the dispersed values $\sigma^2$ after the lapse of the predetermined time period $T_1$, the standard deviation $\sigma$ of the dispersed values $\sigma^2$ is used and when the compared value exceeds this deviation or reference value, it is decided that an etching process is finished. In short, average value m and dispersed ones $\sigma^2$ calculated every etching process can be used as the reference value or threshold on which the end point of etching process is decided by the decision unit 35.

Referring to a flow chart in FIG. 4, it will be described how the end point detecting device 30 is operated. A semiconductor wafer W on which silicon oxide film has been formed is seated on the lower electrode 12 in the process chamber 11 which has been decompressed to a range of 0.1 m Torr—several Torr, for example. High frequency voltage is applied from the high frequency power source 16 to the upper electrode 13 and discharged between the upper 13 and the lower electrode 12. Etching gas whose main component is $CF_4$, for example, is supplied into the process chamber 11 through the gas supply pipe 14 and $CF_4$ and others are made plasma to generate active species. When silicon oxide film on the semiconductor wafer W is etched by these active species, $SiF_4$ and $CO^*$ (monitor species) are produced. Their emission spectra caused when active species such as $CO^*$ return to their ground state pass through the window 17 of the process chamber 11 and come to the photodetector 22 through the lens 21. The photodetector 22 separates the emission spectrum of $CO^*$ (483.5 nm) from the plural emission spectra detected, then photoelectrically converts it into electric signal, which represents light strength I, and sends it, a data signal, to the end point detecting device 30.

Figure 4:
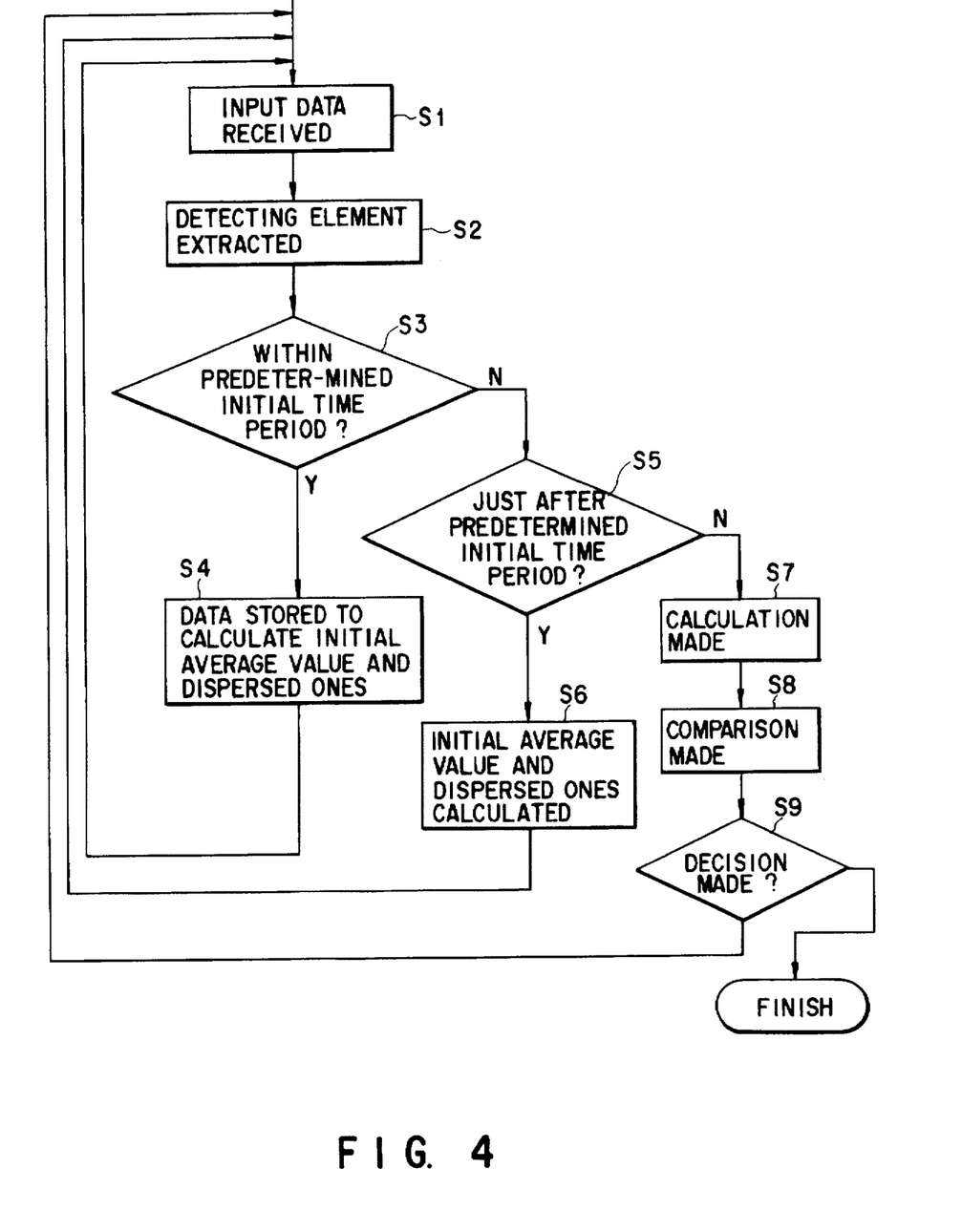
FIG. 4 is a flow chart showing how the end point detecting method according to an embodiment of the present invention is realized by the end point detecting device in FIG. 1.

When the data signal is received by the end point detecting device 30, the following steps are carried out inside the end point detecting device 30, as shown in FIG. 4. The data signal is received as input data by the extractor 31 of the end point detecting device 30 (S1). The extractor 31 extracts those input data which represent light strengths I from the ones received (S2) and confirms whether or not it is within the predetermined initial time period $T_1$ that these input data have been received by the extractor 31 (S3). When the answer is "yes", the extractor 31 sends input data one after another to the arithmetical unit 32, which only stores the input data received (S4). The process then returns to S1 and the above-mentioned steps are repeated to store more and more input data in the arithmetical unit 32. When the answer is "no" at S3, the process advances to S5 and it is confirmed whether or not the predetermined initial time period T1 has passed. When it is confirmed that the predetermined time period $T_1$ has just passed, the average value m and dispersed ones $\sigma^2$ of light strengths I are immediately calculated, on the basis of the input data stored, by the arithmetical unit 32 (S6). The process then returns to S1.

When it is confirmed at S5 that the predetermined time period $T_1$ has passed, signals which represent the average value m and dispersed ones $\sigma^2$ are sent from the arithmetical unit 32 to the arithmetical unit 33 and the comparator 34. The arithmetical unit 33 stores the average value m and calculates the difference of input data received one after another from the extractor 31 relative to the average value m stored (S7). Signals which denote the values of difference are thus sent one after another from the arithmetical unit 33 to the comparator 34. The comparator 34 compares the difference values with the dispersed ones $\sigma^2$ (or standard deviation $\sigma$ in more concrete) already stored (S8) and send results thus obtained to the decision unit 35. Responsive to each of these results, the decision unit 35 decides whether or not the absolute-value of difference exceeds the reference value (S9) and when it does not exceeds the reference value, the process returns to S1 and this decision is repeated. When it is decided at S9 that it exceeds the reference value, the etching process is regarded as coming to its end point and control signal is sent from the decision unit 35 to the control unit 40 to finish the etching process.

According to the above-described example of the present invention, the arithmetical unit 32 receives data signals, which relate to light strengths I, one after another from the extractor 31 and stores them therein within the predetermined initial time period $T_1$ of the etching process. On the basis of these data signals thus stored, it calculates the average value m and dispersed ones $\sigma^2$ of the light strength data. After the lapse of the predetermined initial time period $T_1$, the arithmetical unit 33, the comparator 34 and the decision unit 35 cooperate with one another to decide the end point of etching process on the basis of data signals, or light strengths I, their average value m and dispersed ones $\sigma^2$ received one after another from the extractor 31 and the arithmetical unit 32. Even when etching conditions such as the amount of etching gas supplied are made a little different from the previous ones and the waveform of light strengths I is made unstable by electric noises, as shown in FIG. 3, therefore, the change of light strengths I between the upper and the lower limit at the time of etching process can be clearly distinguished from that at the end point of etching process thanks to electric signals applied from the photodetector 22. This enables the end point of an etching process to be correctly detected to achieve the etching process as desired. It is therefore unnecessary to set a threshold every time etching conditions change. In other words, the present invention enables the end point of an etching process to be correctly and efficiently detected even if etching conditions become different.

In the case of the above-described example, light strengths I of a spectrum caused when activators of plasma P return to their ground state are statistically processed and the end point of etching process is detected on the basis of light strengths I thus statistically processed. However, the present invention is not limited to light strengths. Primary or secondary differential values of a curve which can be drawn while measuring light strengths with the lapse of time may be statistically processed to detect the end point of the etching process. Further, the method and device of the present invention are not limited to the purpose of detecting the end point of an etching process. They may be applied to those cases such as an ashing apparatus where emission spectra change as the plasma process advances.

EXAMPLE 2

In the conventional methods, the end point of etching process is detected using a detecting element. When the detecting element used changes quite a little, therefore, its change is offset by its forced change caused by the change of etching conditions or by electric noises. In short, its true change cannot be distinguished from its forced change, to thereby make it impossible to detect the end point of an etching process.

Figure 5:
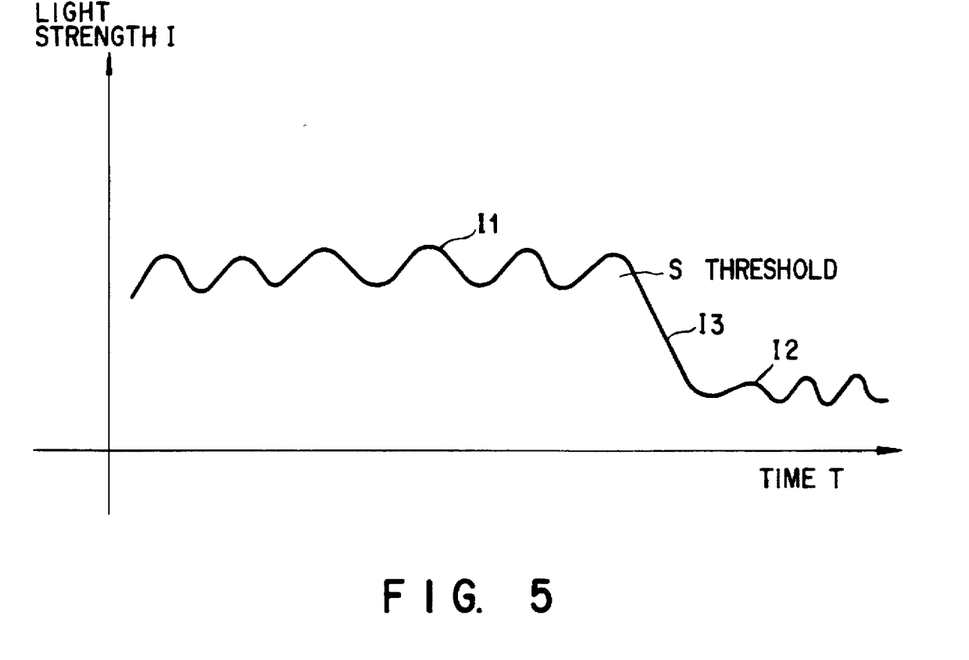
FIG. 5 is a graph showing a light strength waveform of an emission spectrum seen from the start to the end of etching process.

Further, a detecting element such as light strength I is compared, at the time of the etching process, with a threshold previously set. In those cases where the end point of etching process changes every etching process applied, the waveform of light strengths changes drawing plural steps, and it has a convex and concave form because of various layers of different films formed on the semiconductor substrate. Therefore, the end point decision must be repeated every step of it and this makes it more difficult to correctly detect the end point of the etching process. When the light strength I is selected as the detecting element, for example, it is made unstable by changes in etching conditions such as the flow rate of the etching gas, the kind of gas used, pressure and power, as shown by a first waveform $I_1$ at the time of the etching process and a second waveform $I_2$ after the end point of the etching process in FIG. 5. When that threshold s of a third sloping waveform $I_3$ which denotes the end point of the etching process is set adjacent to the start or end of the third waveform $I_3$, therefore, it cannot be distinguished from the first or second waveform $I_1$ or $I_2$. Stable end point decision cannot be made, depending upon etching conditions.

According to the present invention, there can be provided an end point detecting method and a device for the same, said method and device being capable of correctly detecting the end point of an etching process without any influence of electric noises while secondarily detecting any change in light strength, and also capable of continuously and correctly detecting the end point of each etching process applied to each film layer when film layers on a semiconductor substrate are different from one another in thickness.

Figure 6:
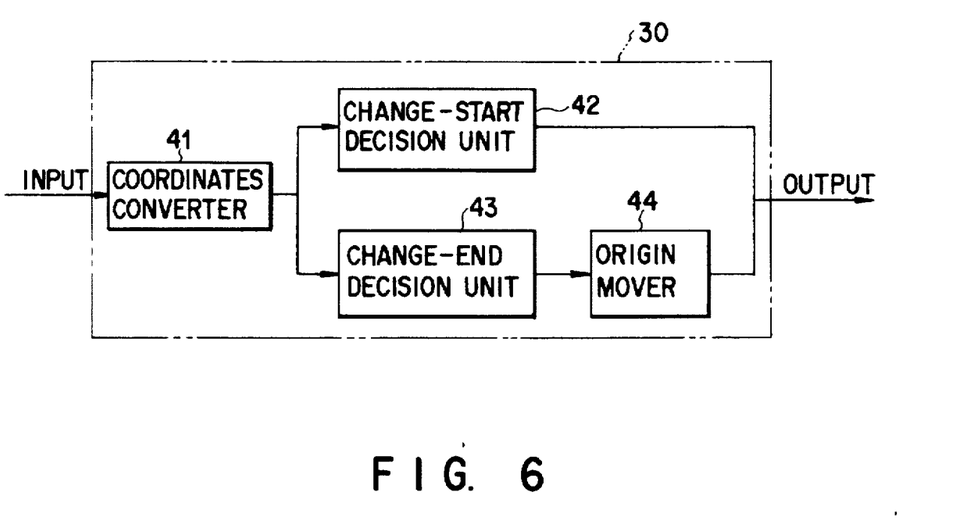
FIG. 6 is a block diagram showing another end point detecting device.
Figure 7:
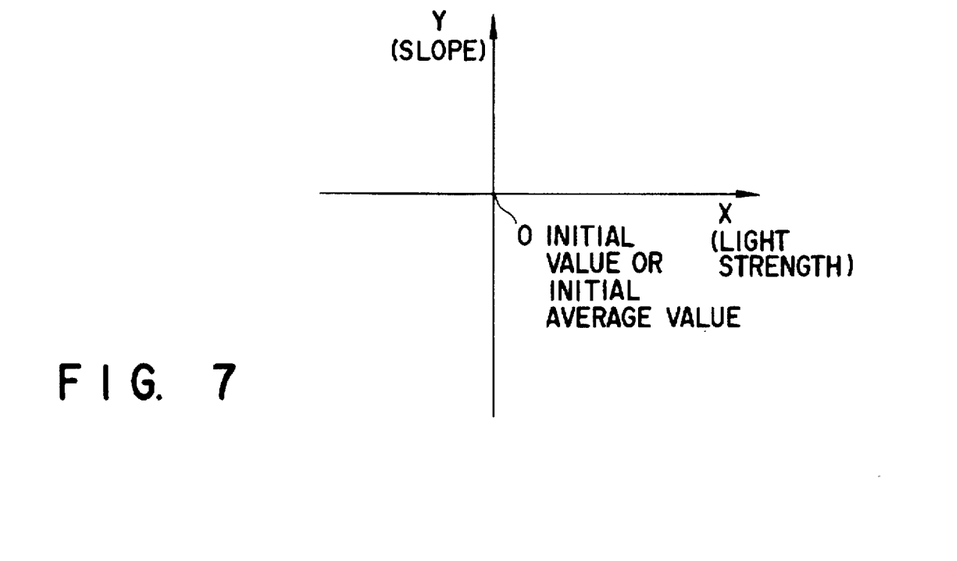
FIG. 7 shows light strengths and their waveform arithmetically calculated by the end point detecting device in FIG. 6 and plotted in X-Y coordinates.
Figure 8A:
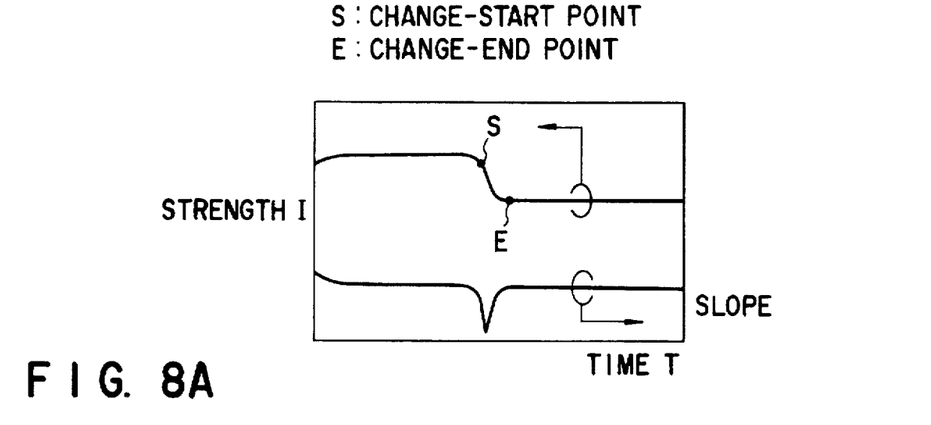
FIG. 8A is a graph showing how light strengths and the slope of their waveform change in a case where film same in thickness is etched.
Figure 8B:
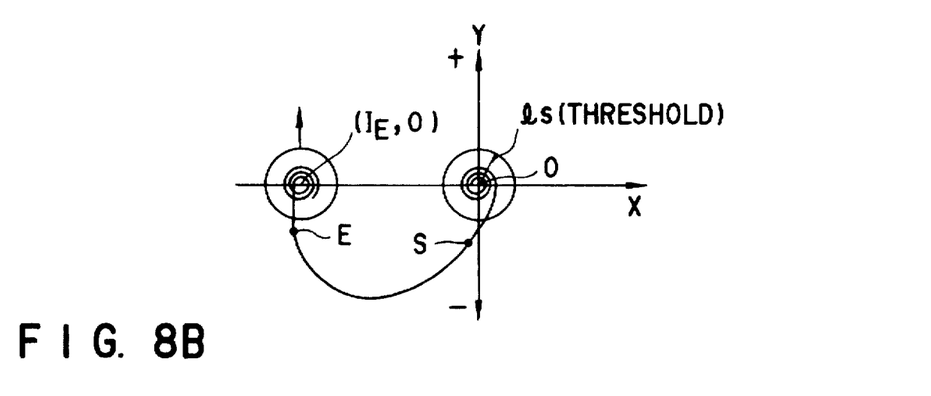
FIG. 8B is X-Y coordinates showing how light strengths and the slope of their waveform in FIG. 8A change.
Figure 10A:
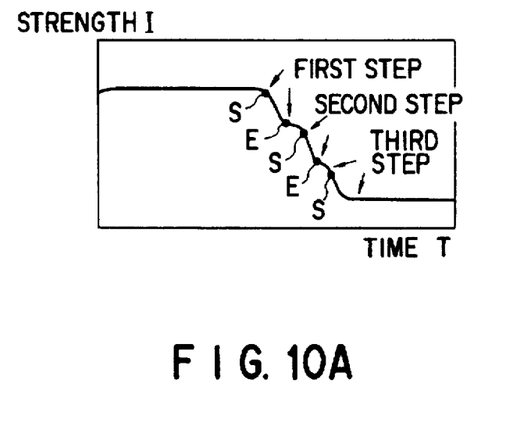
FIG. 10A is a graph showing how light strengths and the slope of their waveform change when film having some areas different in thickness is etched.
Figure 10B:
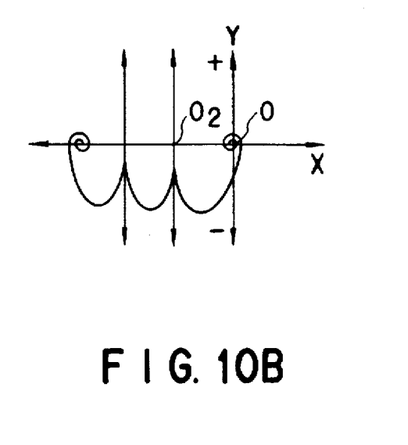
FIG. 10B is X-Y coordinates showing how light strengths and the slope of their waveform in FIG. 10A change.

Another end point detecting device 30 according to the present invention will be described referring to FIGS. 6 through 13. As shown in FIG. 6, it comprises an coordinates converter 41 for plotting light strengths I and primary differential values (or slope) of their waveform in X-Y coordinates, as shown in FIG. 7, using input signals applied from the photodetector 22, a change-start decision unit 42 for comparing the distance l of a then-plotted point from the origin O of the X-Y coordinates with a predetermined threshold ls and regarding that point at which the distance l exceeds the threshold ls as a change-start point S (start inflection point) (see FIG. 8B) of the light strength I and also the end point of an etching process, a change-end decision unit 43 for regarding that point at which then-plotted primary differential values which slope after the change-start point S come near to the X axis or that point at which X coordinates values (or light strength) are left unchanged but Y coordinates ones (or slope) come near to the origin O, as shown in FIG. 8B, as a change-end point E (end inflection point) (see FIG. 8A) of the light strength I and also the end point of the etching process, and an origin mover 44 for setting the finish point decided by the change-end decision unit 43 to be a new origin $O_1$ in the X-Y coordinates, as shown in FIGS. 10A and 10B, and moving the origin O to this new origin $O_1$. The threshold ls is determined by the following equation (I):

$$ls = A \times \sqrt{(Sx^2 + Sy^2)} \qquad (I)$$

wherein Sx is a dispersed value of X (light strength), Sy is a dispersed value of Y (slope), and A is an arbitrarily constant.

Figure 9:
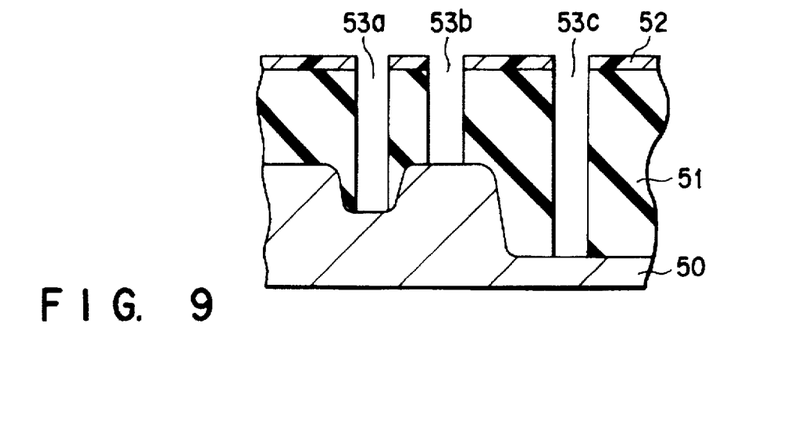
FIG. 9 is a sectional view showing film having some areas different in thickness.
Figure 12:
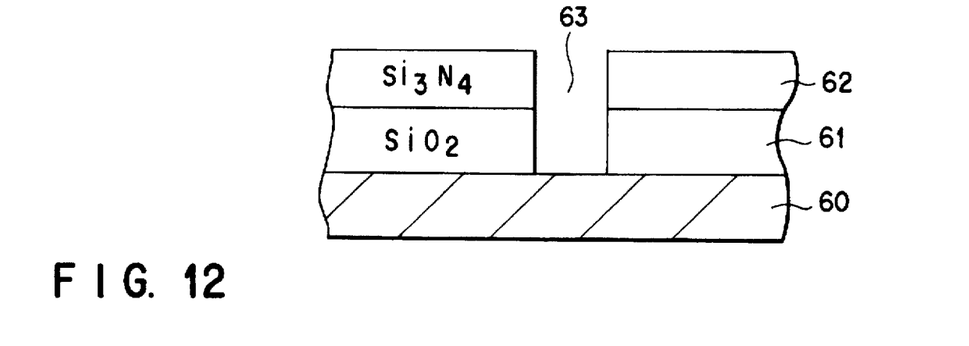
FIG. 12 is a sectional view showing laminated films etched by the end point detecting method of the present invention.
Figure 13A:
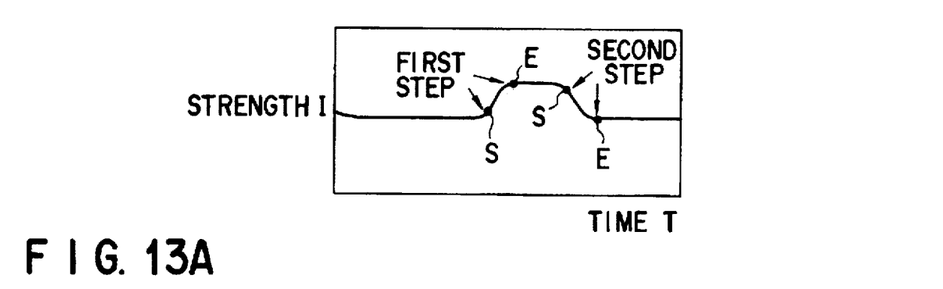
FIG. 13A is a graph showing that the light strength changes like a convex at the time of etching process.
Figure 13B:
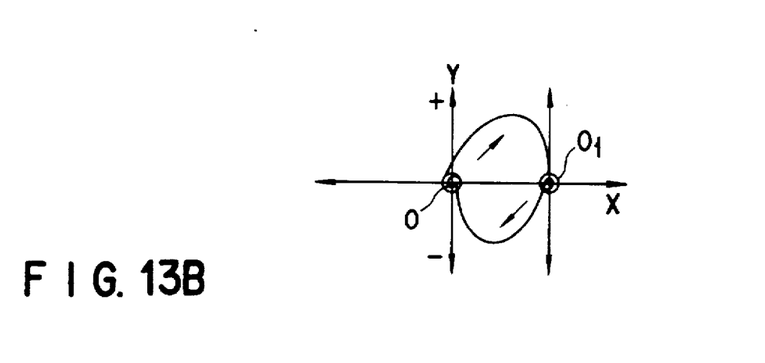
FIG. 13B is X-Y coordinates showing how light strengths and the slope of their waveform in FIG. 13A change.
Figure 13C:
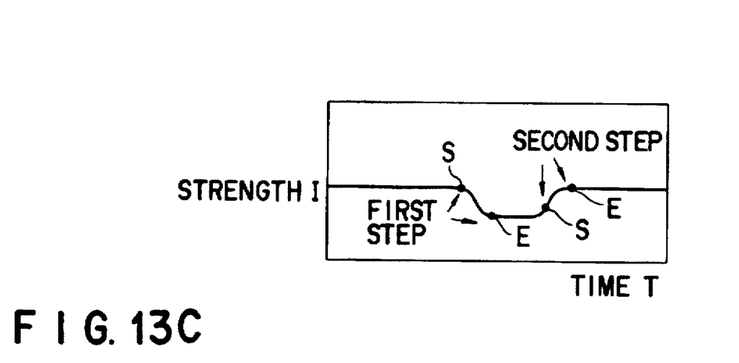
FIG. 13C is a graph showing that the light strength changes like a concave at the time of etching process.

The coordinates converter 41 is intended to convert values of light strength I and slope into X and Y coordinates values, responsive to input signals applied from the photodetector 22, to trace the light strength and the slope in the X-Y coordinates. It is also intended to set the initial values of light strength I and slope or their initial average values for a predetermined initial time period as the origin O of the X-Y coordinates. The predetermined initial time period is a certain time optionally set from the start to the end of etching process. It is a time not depending upon various kinds of etching condition but common to various kinds of etching processes. The change-start decision unit 42 serves to receive a signal applied from the coordinates converter 41 and recognize then-plotted points in the X-Y coordinates. It thus decides the end point of an etching process, as described above, and it sends this decision result to the control unit 40 to control the plasma process apparatus 10. The change-end decision unit 43 serves to receive a signal applied from the coordinates converter 41 and recognize the change-end point E while comprising the slope of then-plotted points (or Y coordinates values) with the threshold (or value as near to the origin O in the Y coordinates axis as possible). It thus decides the end point of etching process, as described above, and it sends this decision result to the origin mover 44. When a layer of film 51 formed on the uneven surface of a substrate 50 is to be etched, while using a layer of resist 51 as a mask, to form recesses 53a–53c each having a different depth in the film layer 51, as shown in FIG. 9, the waveform of light strengths changes drawing a step-like reducing curve or a convex or concave curve, as shown in FIGS. 10A, 13A and 13C, every time the etching of each recess is finished. The origin mover 44 serves to receive signal applied from the change-end decision unit 43 in these cases and move the origin O to a new origin $O_1$ every time the waveform of light strengths changes its curve. When $SiO_2$ and $Si_3N_4$ film layers 61 and 62 formed one upon the other on a semiconductor substrate 60 are etched with etching gas such as a $CH_3+CF_4+Ar+O_2$ gas to form a recess 63 in them, as shown in FIG. 12, the waveform of light strengths I changes drawing a convex curve, as shown in FIG. 13A.

It will be described how the end point detecting method is carried out by the end point detecting device. Emission spectra caused when the semiconductor wafer W is etched with plasma P are detected one after another by the photodetector 22. That one of these emission spectra which has a specific wavelength is selected and the change of its light strength is also used to detect the end point of an etching process in this example. Light strengths I and primary differential values of their waveform are plotted in the X-Y coordinates by the coordinates converter 41, as shown in FIG. 7, and that position at which values then-plotted in the X-Y coordinates begin to remarkably separate from the origin O of the X-Y coordinates is decided to be the end point of the etching process.

More specifically, the origin O of the X-Y coordinates is set using light strengths I (or coordinates values) and their average value for a predetermined time period at the initial etching stage. That position at which the distance l of then-plotted point from the origin O becomes larger than a predetermined threshold ls (see FIG. 8B) can be used as the above-mentioned one at which then-plotted points begin to quickly separate from the origin O. This position is decided to be the change-start point S of light strengths I and also the end point of an etching process by the change-start decision unit 42. At the time of etching process, therefore, light strengths I are not certain but unstable curving up and down, as shown in FIGS. 13A and 13B. As apparent from X and Y coordinates values, therefore, points or values then-plotted in the X-Y coordinates continuously change in a range of the threshold ls, curving like a vortex around the origin O, as shown in FIG. 8B. Just before the end point of an etching process, however, light strength I quickly reduces drawing a slope as shown in FIG. 8A. When X coordinates values (representing the light strength) quickly reduce, values then-plotted in the X-Y coordinates depart from the threshold ls as shown in FIG. 8B. This position is detected and decided to be the change-start point S or the end point of an etching process by the change-start decision unit 42. Then-plotted points which have passed the change-start point S then trace a downward curve downward to the change-end point E in a minus area of Y and X coordinates values, as shown in FIG. 8A. The value of an integral multiple of the dispersed value $\sigma^2$ is preferable to use as the threshold ls.

When the end point of an etching process is detected at the change-end point E, that point at which then-plotted values curving downward from the X axis come again near to it or must to Y=0 is detected and decided to be the change-end point E or the end point of the etching process by the change-end decision unit 43. The change-end point E may be a point at which then-plotted value is smaller than the dispersed value of the slope. After the change-end point E or end point of the etching process, light strengths I become stable at a lower level, although curving up and down. Then-plotted values or points, therefore, trace a vortex-like curve around a coordinate Value ($I_E$, 0).

Figure 11A:
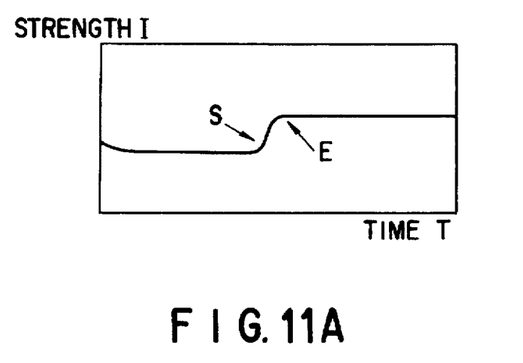
FIG. 11A is a graph showing how light strengths and the slope of their waveform change when film same in thickness is etched.
Figure 11B:
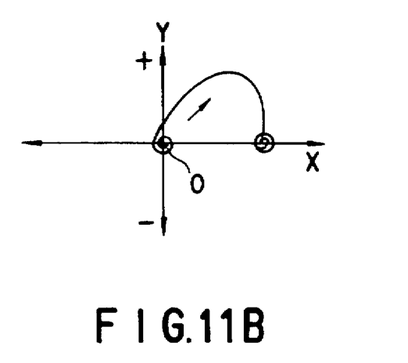
FIG. 11B is X-Y coordinates showing how light strengths and the slope of their waveform in FIG. 11A change.

According to the above-described example of the present invention, a spectrum having a specific wave-length is separated from those spectra which are caused from plasma P at the time of etching process is continuously received and the light strength of this spectrum and the slope of its waveform are plotted in the X-Y coordinates. In short, the end point of an etching is detected using secondary changes in the light strength I and the slope. Any change in the light strength I can be thus secondarily detected from the light strength I and the slope of its waveform at the time of the etching process and the end point of the etching process can be correctly detected without any influence of electric noises. When the specific waveform in plasma P of etching gas is viewed, the light strength I becomes stable at the low level because the gas is consumed at the time of the etching process. After the end point of the etching process, however, gas is not consumed. The light strength I, therefore, rises abruptly and changes as shown in FIGS. 11A and 11B. In this case, however, the end point of the etching process can be similarly detected.

When film 51 which is made different in thickness is etched in the same manner, as shown in FIG. 9, the light strength I reduces like a step every time etching is finished relative to each area of film 51 which is different in thickness from the other areas thereof, as shown in FIG. 10A, because the end point of etching process is attained continuously from the thinnest area of film 51 to the thickest area thereof. This can be seen in a case where various kinds of film each having a thickness different from those of the others are etched in the same manner. Every time the end point of etching process is attained continuously from the thinnest film to the thickest one, the light strength I also reduces like a step. In another case where various kinds of film have same thickness but their areas to be etched are different from one another, etching is finished from film smallest in area to film largest in area. Therefore, the light strength I also reduces like a step, as shown in FIG. 10A, every time the end point of etching process is attained in each film. In a further case where various kinds of film each having a different etching rate are etched in the same manner, same thing can be said. In short, the light strength I also reduces like a step every time etching is finished successively from film largest in etching rate to film smallest in etching rate.

When first etching is finished in the above cases, the end point of the etching is detected, as described above, by the change-end decision unit 43 and detection signal is sent from the change-end decision unit 43 to the origin mover 44. Responsive to this detection signal applied, the origin mover 44 sets a new origin $O_1$ in the X-Y coordinates by using initial average values of light strengths I and the slope of their waveform for the predetermined initial time period, and it moves the first origin O to the new one $O_1$. The end point of this first etching is thus decided from the change-end point E, as described above, and the same process is repeated to successively move the origin to new ones. When all of etchings are finished, the origin mover 44 send end point signal to the control unit 40 to finish the etching process.

Even in a case where the waveform of light strengths I curves convex as shown in FIG. 13A or concave as shown in FIG. 13C, the origin mover 44 receives signal from the change-end decision unit 43 and moves the origin O to a new one $O_1$ every step of the waveform, as shown in FIG. 13B. Then-plotted points draw upward and downward symmetrical curves along the Y axis in this case.

Even when film to be etched has areas different in thickness, the change-end decision unit 43 and the origin mover 44 can cooperate to continuously and correctly detect the end point of an etching process every area of film. Although signal has been sent from the change-end decision unit 43 to the origin mover 44 in this example, it may be sent from the change-start decision unit 42 to the origin mover 44.

Although the present invention has been applied to the etching process, its method and apparatus can also be applied to a case where emission spectra change as the plasma process advances.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of detecting the end point of a plasma process comprising the steps of:

sequentially detecting an emission spectrum of an active species which has a specific wavelength for an initial time period by photodetector means, when an object is processed with a plasma;

obtaining a differential value utilizing a formula such that the differential value represents a relationship between light strengths and time on a basis of information on the emission spectrum of the active species for the initial time period;

obtaining light strengths and corresponding differential values, in a graph wherein the light strengths and the differential values are plotted in X-Y coordinates in which the abscissa shows the light strength and the ordinate shows the differential value, by using information on the emission spectrum of the active species during the process performed after a lapse of the initial time period; and deciding a time at which a position of an obtained light strength and its differential value has separated from the origin of the graph by a distance which exceeds a reference value to be the end point of the plasma process.

2. The end point detecting method according to claim 1, wherein a point at which a position of an obtained light strength and its differential value in the graph intersect the abscissa is set to be a new origin, and a time at which a distance from the position of the obtained light strength and its differential value to the new origin in the graph exceeds the reference value is decided to be the end point of the plasma process.

3. The end point detecting method according to claim 1, wherein a square root of a sum of squares of the dispersed value of the light strengths for an initial time period and the dispersed value of the differential value is the distance to the origin of the graph.

4. A method of detecting the end point of a plasma process comprising the steps of:

sequentially detecting an emission spectrum of an active species which has a specific wavelength for an initial time period by photodetector means, when an object is processed with a plasma;

obtaining a differential value utilizing a formula such that the differential value represents a relationship between light strengths and time on a basis of information on the emission spectrum of the active species for the initial time period;

obtaining light strengths and corresponding differential values, in a graph wherein the light strengths and the differential values are plotted in X-Y coordinates in which the abscissa shows the light strength and the ordinate shows the differential value, by using information on the emission spectrum of the active species during the process performed after a lapse of the initial time period; and deciding an end point of the plasma process as a time at which the distance from the abscissa to the obtained light strengths and differential values are smaller than a reference value after a time at which the obtained light strengths and differential values have separated from the origin of the graph and begin approaching the abscissa.

5. A method of detecting the end point of a plasma process comprising the steps of:

sequentially detecting an emission spectrum of an active species which has a specific wavelength by photodetector means, when an object is processed with a plasma;

obtaining a differential value utilizing a formula such that a differential value represents a relationship between light strengths and time, based on information of detected emission spectrum of the active species for an initial time period;

obtaining an average value and a dispersed value for each of the light strengths and the differential values, for the initial time period, and setting a reference area from the dispersed values of the light strengths and the differential value;

obtaining light strengths and corresponding differential values, in a graph in which the light strengths and differential values are plotted in X-Y coordinates in which the abscissa shows the light strength and the ordinate shows the differential value, by using information on the emission spectrum of the active species in the process performed after a lapse of the initial time period; and deciding a time at which a position of an obtained light strength and its differential value in the graph is outside of the reference area to be the end point of the plasma process.

6. The end point detecting method according to claim 5, further including setting a point at which a position of obtained light strengths and differential values in the graph again intersects the abscissa of the graph as a new origin, and deciding a time at which a distance from a position of obtained light strengths and differential values to a new origin in the graph exceeds a reference value to be the end point of the plasma process.

7. The end point detecting method according to claim 5, wherein a square root of a sum of squares of the dispersed value and the differential value of the light strengths for the initial time period is the distance to the origin of the graph.

8. A method of detecting the end point of a plasma process comprising the steps of:

sequentially detecting an emission spectrum of an active species which has a specific wavelength by photodetector means, when an object is processed with a plasma;

obtaining a differential value utilizing a formula such that the differential value represents a relationship between light strengths and time, based on information of detected emission spectrum of the active species for an initial time period;

obtaining an average value and a dispersed value for each of the light strengths for the initial time period and the differential value, and setting a reference area from the dispersed values of the light strengths and the differential value;

obtaining light strengths and corresponding differential values, in a graph in which the light strengths and differential values are plotted in X-Y coordinates in which the abscissa shows the light strength and the ordinate shows the differential value, by using information on the emission spectrum of the active species in the process performed after a lapse of the initial time period; and deciding an end point of the plasma process as a time in which a distance from the abscissa to the obtained light strengths and differential values are smaller than a reference value after a time at which the obtained light strengths and differential values have separated from the origin of the graph and begin approaching the abscissa.

9. An apparatus for detecting the end point of a plasma process comprising:

emission spectrum detecting means for detecting an emission spectrum of an active species generated in a plasma, which has a specific wavelengths when a process using the plasma is performed for an object to be processed;

calculating means for calculating a differential value utilizing a formula such that the differential value represents a relationship between a light strength and time, on a basis of information on the emission spectrum of the active species for an initial time period;

coordinates converter means for making a graph in which the light strengths and corresponding differential values are plotted in X-Y coordinates in which the abscissa shows the light strength and the ordinate shows the differential value, based on information obtained from the calculating means; and decision means for deciding a time at which a distance from the position of the obtained light strengths and its differential value in the graph to an origin of the graph exceeds a reference value to be an end point of the plasma process.

10. The end point detecting apparatus according to claim 9, further comprising:

second decision means for deciding time at which a position of obtained light strengths and differential values in the graph is separated from the origin of the graph and begins approaching the abscissa and in which a distance from the abscissa is smaller than a reference value to be a second end point of the plasma process.

11. The end point detecting apparatus according to claim 9, wherein the calculating means calculates an average value and a dispersed value for each of the light strengths for the initial time period and its differential values, and sets a reference area from the dispersed values of the light strengths and the differential values.

* * * * *